United States Patent [19]

Eickmann

[11] Patent Number: 4,638,520

[45] Date of Patent: Jan. 27, 1987

[54] TOOTHBRUSH CAPABLE OF MULTIDIRECTIONAL BRUSHING

[76] Inventor: Karl Eickmann, 2420 Isshiki, Hayama-machi, Kanagawa-ken, Japan

[21] Appl. No.: 573,255

[22] Filed: Jan. 23, 1984

Related U.S. Application Data

[60] Continuation-in-part of Ser. No. 421,637, Sep. 22, 1982, abandoned, which is a division of Ser. No. 180,747, Aug. 25, 1980, abandoned.

[51] Int. Cl.⁴ .............................................. A46B 13/06
[52] U.S. Cl. ...................................... 15/22 R; 15/27; 15/167 A; 91/467; 91/470
[58] Field of Search ............... 15/22 R, 97 R; 91/467, 91/470

[56] References Cited

U.S. PATENT DOCUMENTS 4,336,622  6/1982  Teague, Jr. et al. ............... 15/22 R
4,353,141 10/1982  Teague, Jr. et al. ............... 15/22 R

FOREIGN PATENT DOCUMENTS 2702278  7/1978  Fed. Rep. of Germany ..... 15/22 R

Primary Examiner—Edward L. Roberts

[57] ABSTRACT

A toothbrush is provided with bristles to brush and clean the teeth. Since there are cavities between neighboring teeth it is useful to exercise a multidirectional brushing of the teeth and cavities. The handle of the tooth brush is therefor provided with a fluid motor which is driven by fluid, for example by fluid from the water pipe which is available in the living quarters. The fluid motor revolves a rotary member wherein a space with a therein reciprocable piston is provided. The piston rod engages one end of a lever of a transfer arrangement and swings the lever. The other end of the lever then swings the outgoing shaft of the housing. By attaching a tooth brush to the swinging outgoing shaft the brush can do a multi directional movement for better brushing of the teeth and the cavities between the teeth.

3 Claims, 33 Drawing Figures

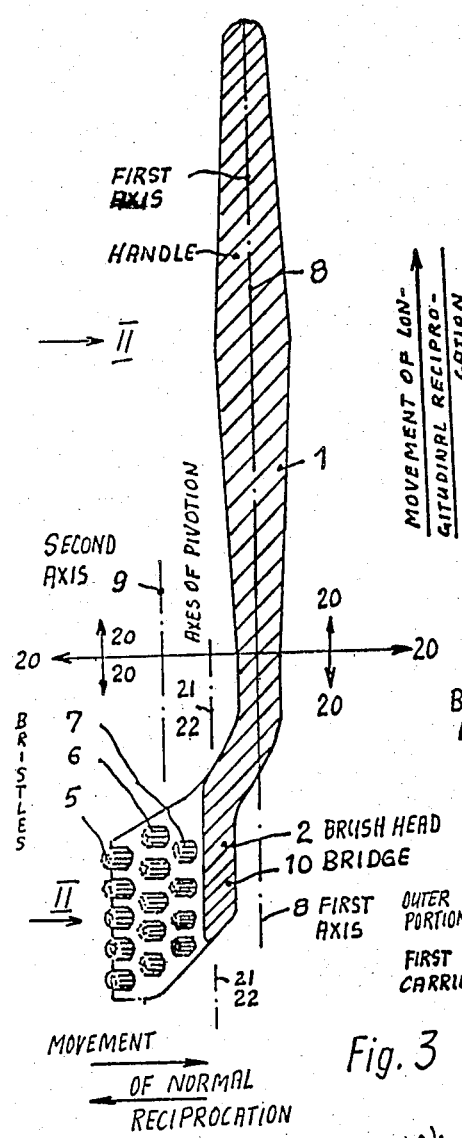
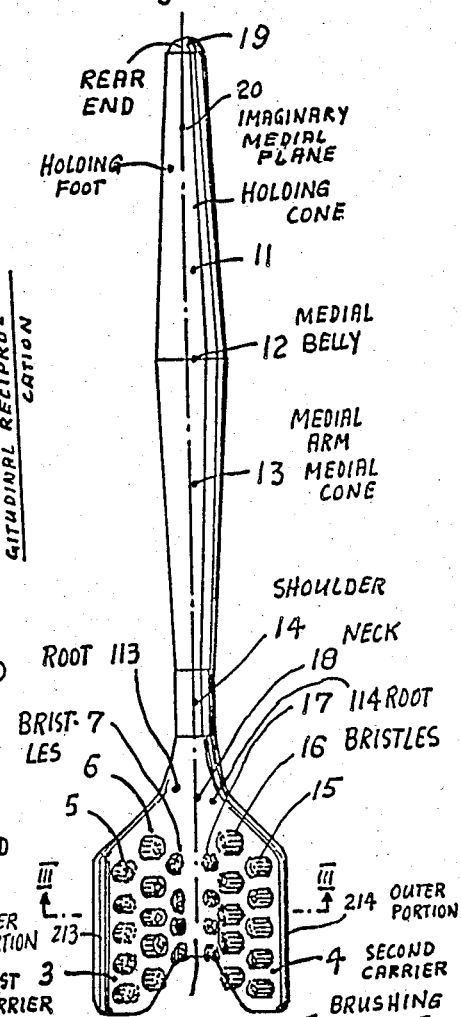
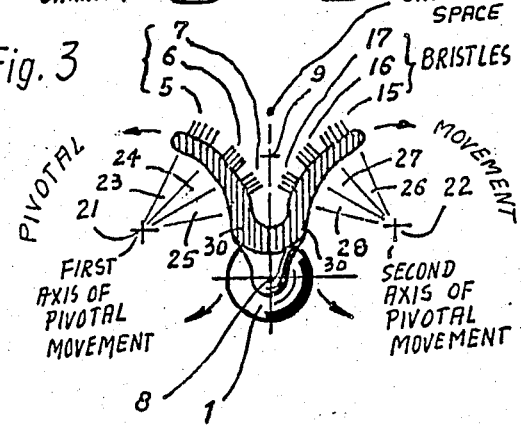

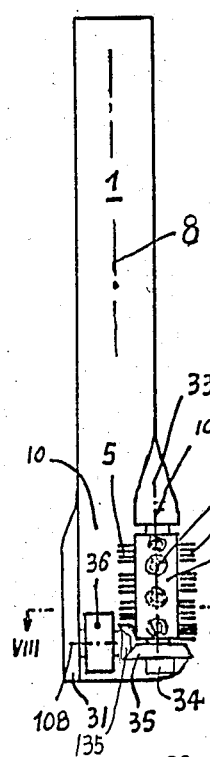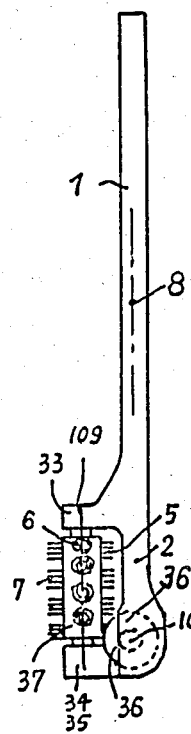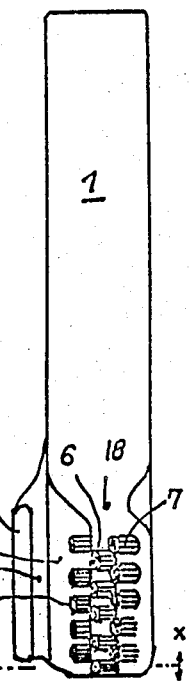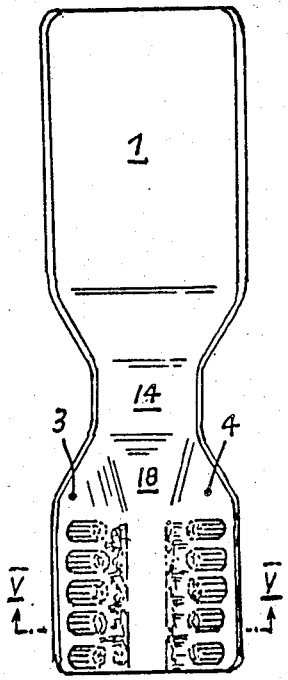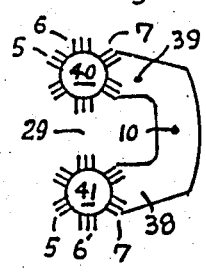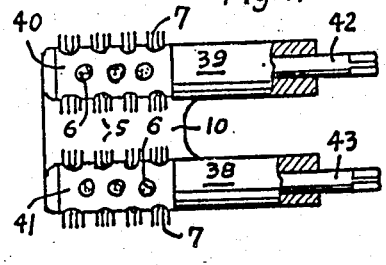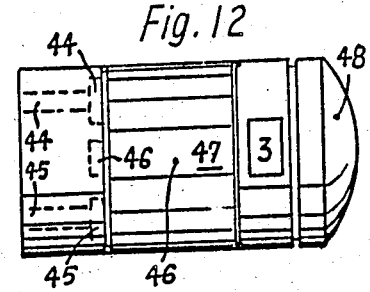

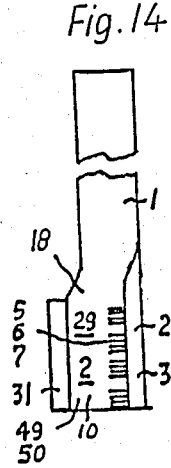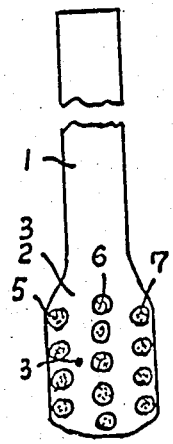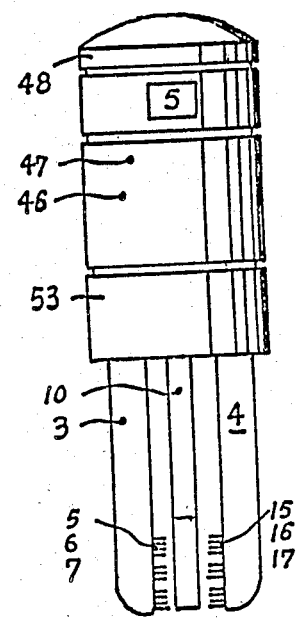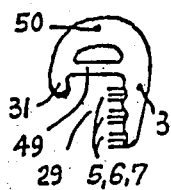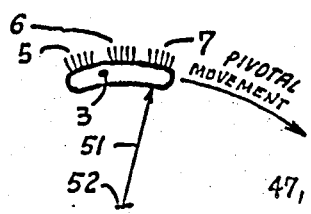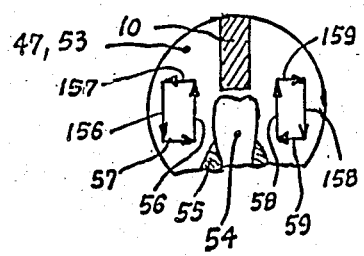

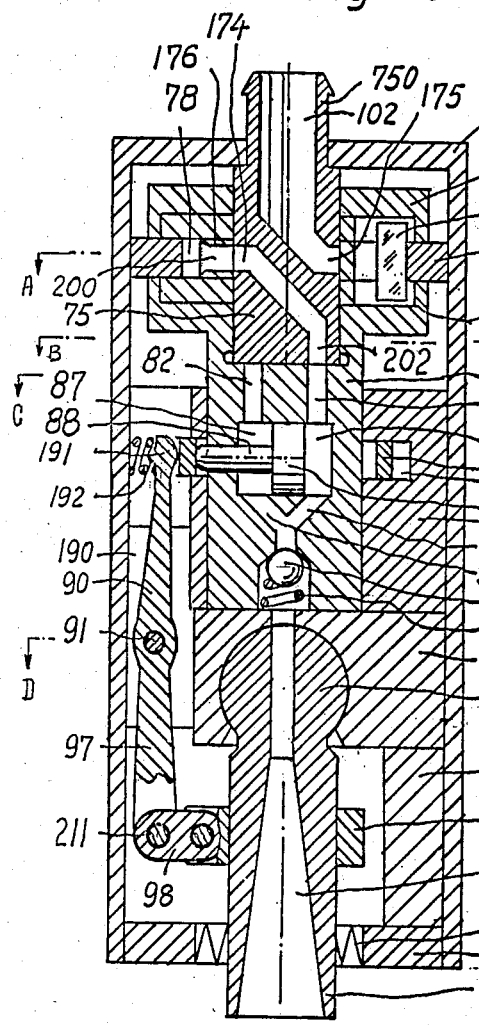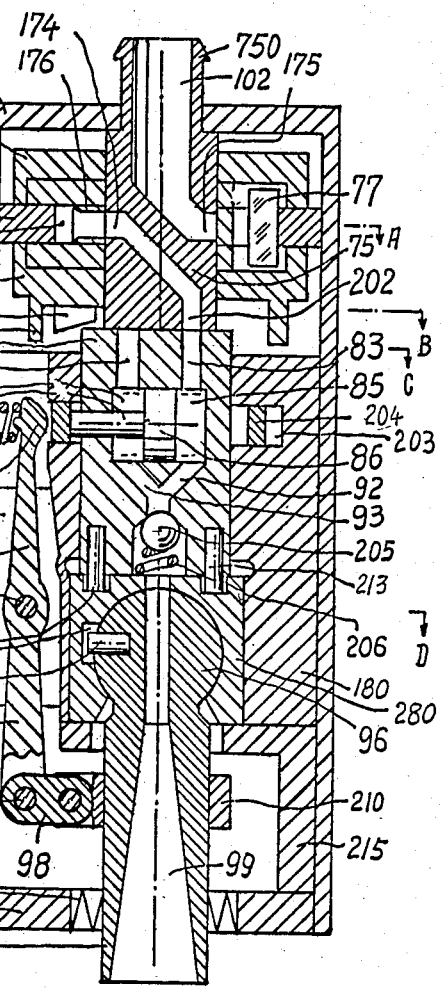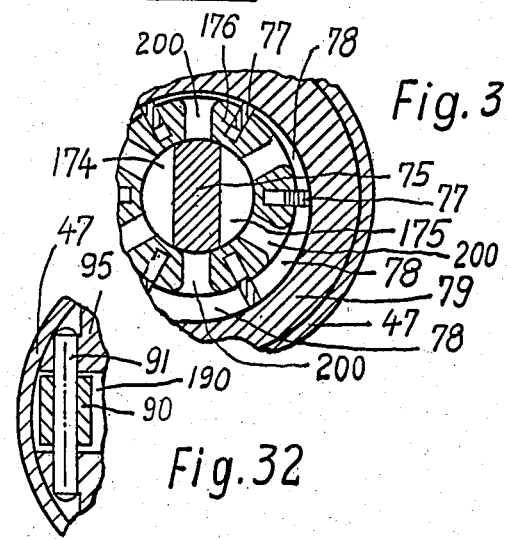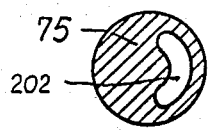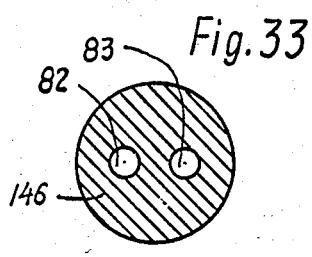

TOOTHBRUSH CAPABLE OF MULTIDIRECTIONAL BRUSHING

REFERENCE TO A RELATED APPLICATION

This present patent application is continuation in part application of my copending application, Ser. No. 06-421,637 which was filed on Sept. 22nd, 1982 and now abandoned.

Application Ser. No. 421,637 is a divisional application of my still earlier application Ser. No. 480,747 which was filed on Aug. 25th, 1980 and which is now abandoned. Priority of Aug. 25, 1980 of application 180,747 is claimed for the present application.

BACKGROUND OF THE INVENTION

1. Field of the Invention

This invention relates to toothbrushes which have a handle and a brush head provided on the handle. The brush head carries bristles for the brushing of teeth, their cavities and for brushing the neighboring gums. The bristles are fastened on carriers, which are provided on the brush head. Toothbrushes in the art have either a single carrier or a plurality of carriers. The single carriers are brushing at a time only one side of the teeth, while toothbrushes with multiple bristle carriers are brushing a plurality of sides of the teeth at the same time or they are at least capable of brushing the tops of the teeth and one side of the teeth at the same time. Or they are capable of moving one or the other of the carriers towards and away from the respective sides of the teeth. This invention includes embodiments which are related to single carrier toothbrushes as well as embodiments which are related to multiple carrier toothbrushes.

2. Description of the Prior Art

The prior art of toothbrushes of the field of the invention is quite crowded by respective patents. Discussed in this specification are only the known prior U.S. patents. The history of toothbrushes is, in short, as follows: Hamilton invented a toothbrush with rectangular carriers and Hamilton obtained U.S. Pat. No. 569,870 for a multiple carrier brush head with rectangular carriers.

Haussmann obtained U.S. Pat. No. 715,263 for multiple carriers, which hold opposed bristles on arched carriers whereby the carriers are able to swing longitudinally around their holding points.

Reynolds obtained U.S. Pat. No. 741,722 with plural carriers with opposed bristles on a twin-armed handle which permitted parallel movements of the bristles and carriers towards each other.

Carrol obtained U.S. Pat. No. 1,133,930 with arched carriers which included bristles under different angles and which could embrace the entire tooth.

Feser got U.S. Pat. No. 1,210,623 for a multiple carrier brush head with parallely arched carriers which are parallel to each other and wherein the arches have radii to conform to the location of plural teeth in the mouth.

Hickmann obtained a patent, U.S. Pat. No. 1,225,955 for plural carriers which bear rotary brushes with axes normal to the carriers.

Paul obtained U.S. Pat. No. 1,254,532 for plural revolving carriers.

Eisner et all got U.S. Pat. No. 1,338,821 for plural revolving carriers.

Mueller got U.S. Pat. No. 1,353,780 for a brush head with plural carriers, wherein the brush head carriers were arranged normally to each other and the carriers were arched outwardly at the front ends.

Carroll was granted his second patent, U.S. Pat. No. 1,389,624 with a twin armed handle made intelligently out of bambo wood and which permitted parallel movements of the bristles to and from each other.

Chicken obtained U.S. Pat. No. 1,409,830 with plural carriers with towards each other extended bristles, with arched configuration of the carriers opening at the front end portion.

Field got U.S. Pat. No. 1,421,199 with twin carriers under a stiff angle.

Metz obtained U.S. Pat. No. 1,507,500 for twin armed carriers.

Ruff got U.S. Pat. No. 1,679,946 for a twin armed brush similar to those of Caroll.

Goldberg obtained U.S. Pat. No. 1,707,113 for a brush head with a medial bridge and therefrom extending two parallel cariers whereby top and sides of a tooth or of plural teeth could be cleansed at the same time.

Davis was granted U.S. Pat. No. 1,908,509, with three carriers.

Trattner obtained U.S. Pat. No. 2,066,241 with shorter carriers than Goldberg.

Boyd obtained U.S. Pat. No. 2,077,392 for triple carriers.

Deutsch also got U.S. Pat. No. 2,214,407 for triple carriers.

Karshmer obtained U.S. Pat. No. 2,263,360 for a twin-carrier brush.

Hart obtained U.S. Pat. No. 2,306,264 for plural revolving carriers.

Ripper obtained U.S. Pat. No. 2,772,624 for triple carrier brushes.

Dinhofer got U.S. Pat. No. 2,807,820 with triple carriers, the medial carrier holding bristles away from those of the other carriers.

Chardiet obtained the grant of French patent No. 1.300.138.

McGee obtained U.S. Pat. No. 3,065,479 for twin carriers;

Rashbaum got U.S. Pat. No. 3,398,421 for triple swingable carriers;

Froideveaux obtained U.S. Pat. No. 3,953,907 for a twin carrier brush; and

Noertheman and Krahn obtained U.S. Pat. No. 4,131,967 for twin carrier brushes.

The most common tooth brush with a single carrier, as still nowadays mostly used, is not mentioned among the above patents and not known to applicant from the history. Thus, the inventor of the most common and simple brush is not known to the present applicant of the present invention.

EVALUATION OF THE PRIOR ART

Of the above mentioned patents of the history of tooth brushes with mostly plural carriers, the patents of Reynolds, Carrol and Ruff, namely U.S. Pat. Nos. 741,722; 1,353,780 and 1,679,946 are in the applicant's view the most intelligent and most practical solutions. Because with simple means a rather effective cleaning of the teeth was obtained by having the ability to thrust the plural carriers towards each other for strong brushing along the teeth.

The remaining patents of the prior art may be grouped as follows:

Patents with twin carriers wherein the carriers are substantially parallel: are: U.S. Pat. Nos. 1,679,946, Ruff; 3,065,479, Mc Gee; 3,953,907 Froideveaux; 715,236, Haussmann; 741,722, Reynolds; 1,210,623, Feser; 1,389,624, Carrol, 1,409,830, Chicken; and 1,679,946, Ruff.

Patents with twin carriers, wherein the carriers are p ovided under an angle: are: U.S. Pat. Nos. 569,870, Hamilton; 1,133,930, Carroll; 1,353,780, Mueller; 1,421,199, Field; 2,263,360, Karshmer and 2,807,820, Dinhofer as well as Noerthemann and Krahn's patent 4,131,967.

Patents with triple carriers, are: U.S. Pat. No. 1,133,930, Carrol; 1,707,113, Goldberg; 1,908,509, Davis; 2,066,241, Trattner; 2,077,392, Boyd; 2,090,663, Booth; 2,772,624, Ripper; 2,807,820, Dinhofer 2,214,407, Deutsch and 3,398,421, Rashbaum.

Patents with plural rotary carriers: are rare, there appeared that of Hickmann of 1917 with two rotary carriers of a good cleaning effect of high merit, namely U.S. Pat. No. 1,225,955; while other patents for plural carriers are U.S. Pat. Nos. 7,254,582; 7,338,821 and 2,306,264 or French patent No. 1,300,138; namely those of Paul, Eisner et all, Hart and Chardiet.

LIMITATIONS OF THE PRIOR ART

As the inventor of the present invention sees it, there is one important provision missing in the history of the toothbrushes of the above mentioned patents. It is a provision to move the bristles of the brush effectively in a direction parallel to the cavities between the teeth and thereby to clean effectively the bottom portions of the cavities and recesses between the neighbouring teeth.

SUMMARY OF THE INVENTION

The main object and aim of the invention is, to provide a toothbrush with multidirectional movement capability to overcome the limitations of the prior art and to provide a brush, which effectively cleans not only the common sides and tops of the teeth, but also the cavities and especially the bottoms of the cavities between the teeth.

One other object of the invention is also, to provide a pivotion of the carrier to effectively clean also along the cavities between the teeth.

Other objects of the invention are to provide specific configurations and locations of the portions or members and means of the toothbrush to obtain the desired better cleaning of the said cavities.

There are a plurality of embodiments provided to the toothbrush of the invention with different means to achieve the desired result or results and aims and they may be provided partially single or in combination with other embodiments of the invention.

The details of some or more of the embodiments of the invention, may for example, be described also as follows:

The arrangement $A_i$ a toothbrush capable of multidirectional brushing for brushing and cleansing of teeth, gums, cavities and recesses between the outer faces of teeth, comprising in combination, a longitudinal handle elongated along a first axis, a brush head forming a bridge and at least one bristle holding carrier, at least partially an inclination between said bristle holding carrier and said bridge, and means to permit at least limited multi-directional movements of said brush head and of said bristle holding carrier, whereon said tooth brush has an imaginary longitudinal plane which extends through said handle, said brush head and said first axis, whereon said tooth brush has a second imaginary axis parallel to said first axis and located in said medial plane, while said second axis may be laid to said teeth to be cleaned by said brush, whereon a brushing space is formed symmetrically of said medial plane and extending from said first axis to and through said second axis, whereon said brush head forms a bridge extending symmetrically along a portion of said medial plane, whereon said bristle holding carrier is extended from said bridge and inclined to said medial plane to form a root on said bridge, a medial portion extending from said root and at least one outer portion remote from said root and extending from said medial portion, whereon bristles are fastened in said carrier to extend from said carrier into said brushing space, whereon said carrier borders said brushing space, whereon said carrier is at least partially inclined at different distances from said bridge under different angles of inclination, particularily at smaller angles of inclination close to said bridge and close to said root but at wider angles of inclination more remote from said bridge and said root and more close to said outer portion, while said bristles are preferred to extend from said carrier at the respective distances under angles normal to said angles of inclination, whereby said brush head can be pivoted in addition to its longitudinal and thereto normally directed movements, in order to at least partially assure the cleaning of said cavities and recesses, in a direction parallel to the extension of said cavities and recesses between said outer faces of said teeth and along the respective mouthskin portions in the neighbourhood of said teeth;

on the toothbrush of arrangement $A_1$ whereon said handle includes an end and a holding foot and, wherein said holding foot provides the possibility to be inserted into a motor-bearing outer body for oscillation or pivotation of said at least one carrier; or the toothbrush of arrangement $A_1$ whereon said handle includes a foot and said foot is provided with radial extensions along the longidtudinal direction of said foot to provide a proper directional holding and pivotion of said tooth brush when cleaning said teeth;

or the toothbrush arrangement B with arrangement $A_1$ wherein said handle has a holding foot adjacent to the rear end of said handle, said holding foot is a cone widening towards a medial belly of said handle, wherein a medial arm extends from said medial belly and forming another cone narrowing in diameter with increasing distances from said belly, while said arm extends from said belly in the opposite direction relatively to said foot, wherein a preferredly cylindrical shoulder is provided on the end of said medial arm and extending therefrom along said first axis, wherein a neck is extending from said shoulder in an inclined direction relatively to said first axis and to said shoulder, and, wherein said neck carries said brush head and said brush head extends with its said bridge parallel to said first axis and through said medial plane;

or the toothbrush of arrangement $A_1$ wherein said handle includes a neck between the main and rear portion and the said brush head which inclines relatively to said first axis locate the rearer portion of said handle around said second portion;

or the toothbrush of arrangement C with arrangement $A_1$ whereon said toothbrush forms an imaginary third axis laterally of said medial plane and below said carrier opposite of said bristles which are fastened in said carrier, wherein said carrier forms an inner portion adjacent to said root and extending from said root under a first inclination and a medial distance from said third axis and parallel to said third axis, wherein said carrier forms a medial portion extending from said inner portion under a second inclination and with said medial distance from said third axis and parallel to said third axis, and, wherein said carrier forms said outer portion extending from said medial portion under a third inclination and with said medial distance from said third axis and parallel to said third axis, whereby said inner portion, medial portion and outer portion are forming angular first, second and third intervall portions around said third axis;

or the toothbrush of arrangement D with arrangement $A_1$ wherein said toothbrush forms an imaginary third axis laterally of said medial plane and below said carrier opposite of said bristles which are fastened in said carrier, and, thereon said carrier is forming an arch plate of substantially equal radius around said third axis, whereby said bristles which are fastened in said carrier are extending substantially in radial directions of said third axis from said carrier, whereby a pivotal movement around said third axis is moving the tips of said bristles along said cavities in a direction parallel to said cavities between said teeth to clean said cavities most effectively at said pivotal movement.

or the arrangement $E_1$ which is a toothbrush capable of multidirectional brushing for brushing and cleansing of teeth, mouth-skin portions, cavities and recesses between the outer faces of teeth, comprising in combination, a longitudinal handle elongated along a first axis, a brush-holding head and at least one brush holding carrier provided and borne on said brush head while said at least one carrier is capable of rotation around a second axis and said provision in said brush head is provided with bearing means to permit said rotation of said carrier, whereon means are provided to guide said brush head along said to be cleansed teeth, and, whereon means are provided to revolve said at least one carrier, whereby said carrier is capable of moving at least partially along the outer faces of the respective to be cleaned teeth in a direction substantially normal to the axes of the respective teeth;

or the toothbrush of arrangement F which includes arrangement E, whereon said carrier is substantially a bar with a substantially cylindrical outer face, whereon bristles are fastened on said carrier to extend from said outer face of said carrier substantially in radial direction of said at least one carrier, and whereby said bristles are capable of entering at least partially into said cavities and recesses between said to be cleansed teeth in order to at least partially brush said cavities and recesses in a directional movement substantially at least partially parallel to the axes of said teeth.

or the toothbrush of arrangement $G_1$ with arrangement E wherein said at least one carrier is of an at least partially deformable plastic material, whereby said carrier is capable of brushing with its outer face the respective outer face of the tooth in question;

or the toothbrush of arrangement $H_1$ with arrangement $E_1$ whereon said means to guide said brush head on said teeth is a bridge extending along said brush head, wherein said brush head forms at least one lateral member located laterally of said medial plane and extending from said brush head in a direction substantially laterally of said medial plane, and, wherein said at least one carrier is borne in said lateral member;

or the toothbrush of arrangement $J_1$ which includes arrangement $H_1$ whereon said means to revolve said carrier is a roller which is borne in said bridge to be capable to revolve around its roller-axis and said roller has an outer face to be capable to roll along the respective portion(s) of the respective tooth(teeth), and thereby to touch said respective portion of said tooth to be set into rolling motion when said roller moves along said portion of said tooth, wherein a gear means is provided to extend from said roller to said carrier to drive said at least one carrier when said roller rolls along said portion of said tooth or portions of said teeth, whereby said carrier moves at least partially at least indirectly along the respective portion of said tooth (teeth) or said cavity (ties) or recess(es) in a direction substantially normal to the axis (axes) of the respective tooth (teeth) when said brush head moves in a direction substantially parallel to the direction of said axis and handle along said teeth, while an overlaying multi-directional movement along the gums and outer face of the respective tooth can be provided if so desired;

or the toothbrush of arrangement $K_1$ which includes arrangement $E_1$ whereon a rotary motor is housed in an outer body which carries at least a shaft which extends to said brush holding carrier and at least indirectly connects to at least a portion of said carrier to engage at least said portion of said carrier, whereby said rotary motor transfers its rotary motion to said at least one carrier;

or the toothbrush of arrangement $L_1$ with arrangement $K_1$ wherein said carrier holds bristles in a direction substantial radial of said carrier, whereby said bristles revolve along said teeth to brush said teeth, said mouth skin and said recesses in a direction parallel to the extension of said cavities and recesses;

or the toothbrush of arrangement M with arrangement $K_1$ wherein said rotary motor is provided with an electronic control device and said handle contains setting devices for defining the speed or timing of said control device;

or the toothbrush of arrangement $N_1$ which includes arrangement $E_1$ whereon said brush head forms at least two lateral members extending substantially laterally from said brush head and laterally to said medial plane, whereon said brush head forms a bridge extending along said medial plane to guide said brush head along the to be cleaned teeth, wherein said carriers are substantially bars with cylindrical outer faces and are revolvable borne in said at least two members, whereon at least each one member of said members is symmetrically located opposite relatively to the other of said members and relatively to said medial plane, wherein one of said members bears one of said carriers, another of said members bears another of said carriers, and, wherein said rotary motor is provided with transmission means to revolve said at least two carriers;

or the toothbrush of arrangement $O_1$ which includes arrangement $E_1$ wherein said handle contains a chamber, said chamber contains at least a teeth-health medicine and a passage from said chamber to port into said carrier wherein said motor is connected to means to at least temporarily, stepwise or continually transfer at least defined portions of said teeth-health medicine to and through said carrier to supply it respectively to the to be cleaned portions of said teeth, cavities, recesses and gums;

or the toothbrush of arrangement $P_1$ which includes arrangement $O_1$ wherein said handle contains a second chamber for the reception and containment of a fluid, wherein said chambers are communicated to passages which communicate to each other, and, wherein said motor is provided with means to press said medicine and said fluid in properly to each other related portions through said passages and carriers to said teeth, cavities, recesses and gums when said toothbrush is used to clean or cleans said teeth, cavities, recesses and gums;

or the toothbrush of arrangement $Q_1$ with arrangement $P_1$ wherein said motor is provided with control means and said handle with a setting means for the adjustment of said control means, and, wherein said setting means is capable of a predetermined or variable setting of said control means to define the rotary speed of said carrier and the quantities and advance ratios of said medicine and of said fluid;

or the toothbrush of arrangement $R_1$ which includes arrangement $D_1$ whereon said handle includes an elongated rear and main-portion extending parallel to said first axis and to said third axis and substantially along a fourth axis through the middle of said arch plate of said carrier and thereby substantially along the middle between said first and third axes, whereby the holding portion substantuated by said rear and main portion of said handle provides the center axis of through said arch plate for effective and convenient brushing of said cavities between said teeth;

or the toothbrush of arrangement S with arrangement $R_1$ whereon said handle includes a rear portion and an outer body is associated to said tooth brush, wherein said outer body houses a motor and contains a holder, wherein said holder retains and holds said rear portion of said handle, and, wherein said motor drives said pivotion of said tooth brush around said fourth axis, when said toothbrush is held in the hands of the person who cleans its teeth and said motor is set to run and to drive said pivoting and thereby said pivotal movement for cleaning of said cavities between said teeth;

or the toothbrush of arrangement $T_1$ which includes arrangement $K_1$ wherein said rotary motor is a fluid motor, wherein said outer body is provided with an entrance port to make it possible to connect said entrance port by a flexible hose to the water pipe in the bathroom where the cleaning of the teeth occurs, and wherein said entrance port communicates to said motor, wherein said hose transfers water from said pipe to said motor and through said motor, whereby said motor is revolved, and, wherein an exit port extends from said motor into a passage through said handle and through said carrier, whereby said water flows through said bristles towards said teeth, cavities, recesses and skin, when said motor is revolved and said teeth are brushed by said toothbrush;

or the toothbrush of arrangement $U_1$ which includes arrangement $K_1$ wherein said motor provides vibrational reciprocation of said carrier in a direction parallel to said bristles and towards and away from said teeth, cavities, recesses and skin, or the toothbrush of arrangement $V_1$ which includes arrangement $A_1$ wherein said rootes are flexible relatively to said bridge, wherein said bridge is provided with an outer holding angle, whereby said holding angle and said bridge can be guided along said teeth and lateral dislocation of said bridge away from said teeth is prevented by said holding angle, whereby said holding angle acts as a guiding bar, wherein said carrier is pivotable around said root by said flexibility of said root, wherein a thrust-transfer means is associated to said carrier and to said bridge, and, whereby thrusting movements on said bridge in a direction towards said teeth are transferred by said transfer means to said carrier to pivot said carrier in a direction substantially normal to the direction of said thrusting movements toward the side of said teeth and into the cavities between said teeth to enter said cavities with force and to move along said sides of said teeth with a force which is determined by the force of said thrusting movements on said bridge;

or the toothbrush of arrangement $W_1$ which may include arrangement $A_1$ and is a toothbrush capable of multi-directional brushing for brushing and cleaning of teeth, gum portions, cavities and recesses between the outer faces of teeth, comprising in combination, a longitudinal handle elongated along a first axis, a brush head forming a bridge and two bristle holding carriers, at least partially an inclination between said bristle holding carriers and means to permit at least multi-directional movements of said brush head and of said bristle holding carriers, whereon said tooth brush has an imaginary longitudinal plane which extends through said handle, said brush head and said first axis, whereon said tooth brush has a second imaginary axis parallel to said first axis and located in said medial plane, while said second axis may be laid to said teeth to be cleaned by said brush, whereon a brushing space is formed symmetrically of said medial plane and extending from said first axis to and through said second axis, whereon said brush head forms a bridge extending symmetrically along a portion of said medial plane, whereon said bristle holding carriers are extended from said bridge symmetrically to said medial plane to form roots on said bridge medial portions extending from said roots and outer portions remote from said roots and extending from said medial portions, whereon bristles are fastened in said carriers to extend from said carriers into said brushing space, whereon said carriers border said brushing space, whereon said carriers are at least partially inclined at different distances from said bridge under different angles of inclination, particularily at smaller angles of inclination close to said bridge and close to said roots but at wider angles of inclination more remote from said bridge and said roots and more close to said outer portions, while said bristles are preferred to extend from said carriers at the respective distances under angles normal to said angles of inclination, whereby said brush head can be pivoted in addition to its longitudinal and thereto normally directed movements in order to at least partially assure the cleaning of said cavities and recesses in a direction parallel to the extension of said cavities and recesses between said outer faces of said teeth and along the respective gum portions in the neighborhood of said teeth;

or the toothbrush of arrangement $X_1$ which includes arrangement $W_1$ whereon said handle includes a rear portion of a configuration of a cone which widens towards a medial belly and ends in a part-ball formed rear end, whereby said rear portion of said handle forms an insertion-element, whereon on outer handle includes a hollow reception cone of a size complementary to said cone of said rear portion of said handle, whereby said rear portion and insertion element can be inserted and kept in said hollow reception cone of said outer handle.

wherein said outer handle houses a motor which is connected to a transfer means through said handle to said carrier, whereby said motor is capable of providing at least one direction of motion to said carriers;

or the toothbrush of arrangement $Y_1$ which includes arrangement $X_1$ wherein said motor provides a pivotal movement to said carriers;

or the toothbrush of arrangement $Y_1$ wherein said motor provides in addition to said pivotal movement a second movement parallel to the extension of said cavities between said teeth;

or the toothbrush of arrangement $Y_1$ wherein said motor provides to said carriers in addition to said pivotional movement a third movement in the direction normal to the extension of said cavities and of said outer faces of said teeth;

or the toothbrush of arrangement $Y_1$ wherein said motor provides to said carriers in addition to said pivotal movement a fourth movement in the direction parallel to the extension of said shaft and thereby parallel to said first axis;

or the toothbrush of arrangement Z which includes arrangement $W_1$ whereon said handle extends along said first axis, while said first axis extends through said second axis and said handle includes lateral extensions normal to said medial plane, whereby the movements of said brush head can be effectively controlled by the hand of the person who is engaged in cleaning its teeth.

Another aim and object of the invention is also to provide a rather simple brush with a brush head of a cross-sectional configuration, very suitable to move the bristles from the bottoms of the cavities between neighboring teeth, along the skins of the teeth and along the cavities, to clean them effectively.

For that purpose the carrier of the brush head has backward inclinations towards the sides of the medial portion of the carrier with bristle tufts rows along the carrier to assure, that the bristles have, at all times or mostly during the movement along the teeth and the cavities the proper angle of attack relatively to the skin and the teeth as well as to and in the cavities between the teeth.

Care is taken for the better cleaning of the rootes of the teeth and of the cavities between them by the respective setting of a greater number of bristle tufts at the outer portions of the carriers and less bristle tufts at the root-near portions of the carriers. This is done, because too great a number of bristle tufts makes the cleaning of the bristles more difficult. Since cleaning should be done fast without elongating the time required to brush the teeth, the invention considers, that the number of tufts and rows of bristels should be carefully planned and not exceed the requirement. But they should be placed properly to obtain the maximum of effect of brushing and cleaning under proper angles of attack and on the correct places of brushing and cleaning.

When considering the many embodiments and figures of the application, it is possible to recognize and notice, that one of the major achievments by single embodiments or figures or by combination of figures or of parts or of embodiments of the invention, are consisting therein, that the movements are improved, that means are provided to add a proper pivotal movement of the carrier along the cavities and the teeth in order to obtain a better cleaning and brushing of the, skin, teeth and cavities between teeth with proper angles of attack of the bristles along the teeth, skin and cavities during the operation of cleaning and brushing said teeth, cavities and skin.

The above described aims and objects of the invention are considered to be patentable as claims, if written in the form of claims. Since a single patent application is however supposed to deal in the claims with a single specie, the above mentioned embodiments, aims and objects of the invention will be claimed in divisional applications or in continuation applications of the parental or of the present applications. All these claims were submitted in the parental application under the priority date of the parental application. Most of them have been withdrawn from consideration in the parental application, after a single specie was elected.

The present application will in its claims deal with the specie of FIG. 28, however it will include the possibility of operation of the carriers of FIGS. 6 to 10 by the motoring means of FIG. 28 or FIG. 29.

BRIEF DESCRIPTION OF THE DRAWINGS

FIG. 1 is a longitudinal sectional view through one embodiment of the invention.

FIG. 2 is a view onto FIG. 1 along the arrows II, II.

FIG. 3 is a cross-sectional view through FIG. 2, along the line III—III.

FIG. 4 is a view onto another embodiment of the invention.

FIG. 5 is a cross-sectional view through FIG. 4 along the line V—V.

FIG. 6 is a view onto another embodiment of the invention.

FIG. 7 demonstrates FIG. 6 in a view onto it, under an angle normal to FIG. 6.

FIG. 8 is a cross-sectional view through FIG. 6 along the line VIII—VIII.

FIG. 9 is a view onto a further embodiment of the invention.

FIG. 10 is a cross-sectional view through FIG. 9 along the line X—X.

FIG. 11 is a view onto still a further embodiment of the invention, partially in longitudinal sectional views.

FIG. 12 is a view onto an outer handle, mountable to FIG. 11.

FIG. 13 is a view from the front onto FIG. 11.

FIG. 14 is a view onto still another embodiment of the invention.

FIG. 15 is a view onto still a further embodiment of the invention.

FIG. 16 is a view onto still another embodiment of the invention.

FIG. 17 is a view from the front onto FIG. 17.

FIG. 18 is a view from the front end onto FIG. 15.

FIG. 19 is a view from bottom onto FIG. 16 and includes a schematic.

FIG. 28 is a longitudinal sectional view through a motor containing and controllers containing outer handle of the toothbrush of the invention.

FIG. 29 is a modification of FIG. 28;

FIGS. 30 to 33 or sectional views through FIGS. 28 and 29 along the arrowed lines A—A, B—B, C—C and D—C respectively therein.

DESCRIPTION OF THE PREFERRED EMBODIMENTS

Figure 20:
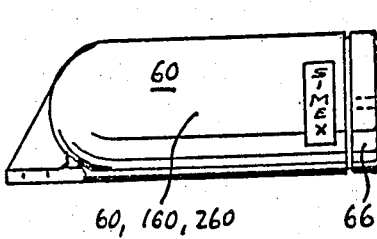
FIG. 20 is a view from the side onto still a further embodiment of the invention, partially in longitudinal sectional view.

In FIGS. 1 to 3 and some of the other figures, the toothbrush has a handle 1 and a brush-head 2. An imaginary medial plane can be assumed to lay through the longitudinal axis 8 and it is explained in FIG. 1 by the cross-arrows 20 and also visible in FIG. 2, where it runs normal to the sheet of the paper, whereon the figure is drawn. It should be noted, that the described imaginary medial plane 20 forms the basis for this and many others of the Figures and for the embodiments described in this and some of the other figures. For manufacturing and in the design drawings everything is designed and made in relation to the described imaginary medial plane 20 which runs through the toothbrush and is therefore no longer visible to the eye, when the toothbrush is actually produced.

Handle 1 ends in the bridge 10 of brush head 2. Bridge 10 may be normally extending relatively to the medial plane 20. It may also be distanced from the longitudinal medial axis 8 of the medial plane 20 and handle 1. It may extend parallel to the mentioned medial axis 8 of the handle 1.

From the lateral ends of the bridge 10 the bristle tufts carriers 3 and 4 are extending upwards to form a brushing space 29 therebetween. Thereby the carriers 3 and 4 are boardering the brushing space 29. The bristles may be arranged in bristle tufts 5,6,7 and 15, 16, 17, parallel to each other, but distanced, in lines 5,6,7 and 15, 16, 17, from each other. Bristles 5,6,7 on one of the carriers, and bristles 15, 16, 17 on the other of the carriers 3,4.

The speciality of this embodiment of the invention is, that the carriers 3 and 4 are not parallel in the sectional view of FIG. 3, as usual in the elder patents of for example, Haussmann, Reynolds, Ruff, Deutsch, Carrol, Boyd, Ripper, Goldberg, and Froideveaux, and also not normal to each other as in the patents of for example, Rashbaum, Hamilton, Mueller, Karshmer and like; and they are also not extending under a V-form as in the patents of Field, Dinhofer and Noertheman-Krahn, but in the specific arrangement of the present invention.

That is, that the carriers 3 and 4 at their roots on their extension from the bridge 10 are extending parallely to each other upwards along the brushing space 29 under an angle of zero degrees between them. Thereafter they are inlining under a first angle relatively to each other, whereby the gap between them, the brushing space 29, is widening. This is followed by a next portion, one of the medial portions, by a still wider second angle between them, which widens the gap and brushing space further. The first angles and second angles are medial angles and are forming the medial portions of the carriers 3 and 4. The second angle range is followed by the outer portions which are forming a third angle between the portions and thereby a still wider angle and wider gap and brushing space 29. The inclinations of the mentioned portions of the carriers with the zero-angle or angle between the roots, the first, second and third angles of first, second and third inclinations of the root-portion, medial portions and the outer portions are preferred to be made symmetrically relatively to the mentioned imaginary medial plane 20.

FIG. 3 also shows, that the mentioned inclinations of the carrier portions of carriers 3 and 4 may be defined by a first, second and third portion 23,24,25 around an outer axis 21 by carrier 3 and by first, second and third portions 26,27,28 around a second outer axis 22 by carrier 4. The outer axis 21 and 22 are preferred to be parallel to each other and to be parallel to the mentioned medial plane 20 and to the axis 8. They may be distanced from the medial longitudinal axis 8 to form between them an imaginary normal medial plane 21, 22, normal to the mentioned imaginary medial plane 20. In FIG. 1 the referential 21, 22 define this normal plane and the outer axes 21 and 22 are located in this normal plane 21, 22. The normal plane and the outer axes are again imaginary matters, important for the actual designing and production of the toothbrush, but they are not visible to the eye, when the brush is actually produced.

The outer axes 21 and 22 are an important matter for the understanding of this present invention. As already reported in the earlier part of this application, it is important, to clean the roots of the cavities between the respective neighboring teeth. For this purpose, the brush of the invention is pivoted around axis 22 when bristles 15 to 17 are led against the respective teeth and cavities. The pivotal movement is shown in FIG. 3 by the respective arrows. When cleaning for example, upper teeth in the mouth, the carrier 4 is pivoted along the teeth and cavities in the direction of the bottom right arrow in FIG. 3. The top arrow on the right side of FIG. 3 shows the returning motion of the brush into its outgoing starting position, whereby at the return motion the carrier 4 may move slightly away from the teeth and cavities. The operation of the carrier 3 with bristles 5,6,7 is done similarly at the respective other side of the respective teeth. When cleaning bottom teeth in the mouth or lower jaw, the brush is approximately 180 degrees turned and the cleaning similar repeated.

Axis 9 through medial plane 20 and seen in FIGS. 1 and 3 is the axis through the brushing space 29. It is parallel to axis 8 and normal plane 21,22, when the brush head is actually made as shown in FIGS. 1 to 3.

While the pivotal movement around the first axis of pivotal movement, 21, and the second axis of pivotal movement, 22, is explained, it should be noted, that the usual movement of longitudinal reciprocation may be exercised in addition to the (novel) pivotal movement. This is shown by the respective arrows in the figures of this sheet of the drawing. In addition the normal movement which is normally directed relatively to the mentioned movement of longitudinal reciprocation, may be done, if so desired. Thus, the brush of this embodiment of the invention is not limited to the pivotal movement but the commonly known movements can also be done and actually there may be exercised an overlaying of the mentioned movements of longitudinal reciprocation, normal reciprocation and pivotal reciprocation or pivotal movements.

In this respect it should be recognized, that the known U-shaped brush heads of the prior art, for example those, which are mentioned in this present application, can not permit the pivotal movement of the invention. Because the U-shape of to each other parallel plates or carriers holds the brushes of the former prior art all times parallel to the axes of the respective teeth. When an inclination or pivotal movement would be done by force, the bristles would be bent and they would thereby loose their ability to clean with their tips. They would merely slide along the teeth with their longitudinal skins. A cleaning could then not be effective.

Recognition is requested to the fact, that a pure normal movement would hurt the skin at the moment of begin of touching the skin in the neighbo of the teeth and it would also hurt the outer skin of the teeth. A pure normal movement can therefore not be the final solution of teethbrushing or teeth cleaning, neither from medical views nor from views of convenience or efficiency of cleaning.

Of interest is also, that the commonly known single bar straight toothbrush also rarely is capable of a pivotal movement. It has no configuration and no guide for it, whereby it becomes difficult to exercise the pivotal movement. And, even, when under great effort a pivotal movement would be exercised, there would not be the second and third row of bristle tufts of the carriers of the brush of this embodiment of the invention. They are repeating at the pivotal movement the first cleaning by a second and third cleaning, what the flat bar brush with the single row of tufts can not do. For the single flat plate brush it is also very delicate to direct a pivotal movement, even when such pivotal movement would be recommended. Because for an effective cleaning, the pivotal movement should be combined with the proper angle of attack relatively to the teeth. That is accomplished by the brush head with the multiple inclinations of the carriers of the brush of the invention, but it is difficult to obtain such result with one or the other of the brushes of the prior art.

Figure 26:
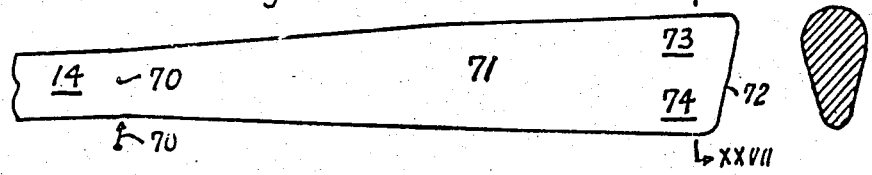
FIG. 26 is a view from the side onto still another handle of the invention.
Figure 27:
FIG. 27 is a cross-sectional view through FIG. 26 along the line XXVII—XXVII.

FIGS. 26 and 27 demonstrate an alternative of a handle. It has the usual shoulder 14 of the invention with the therefrom extending main portion 71. Between them the softening radius 70 may be provided. Gradually along the extension from the neck towards the rear end 72 the handle transforms into a cross-sectional configuration as shown in FIG. 27 and which defines a wider upper portion 73 and a narrower bottom portion 74. The end may be inclined by an inclination 72. This crossectional and outer configuration of the handle is provided to have a proper grip on the handle when operating the brushing of the teeth and when directing the movement directions of the brush head including the pivotal movement along the teeth and cavities as explained by this invention.

The handle 1 in FIGS. 1 to 3 has a rear end 19 or end 19 for example of the form of a half ball. From it the holding foot extends towards the medial belly 12 as a cone or holding foot 11, which widens gradually in diameter from the rear end 19 towards the medial belly 12 to obtain the biggest diameter at the medial belly 19. From the medial belly 12 extends parallel to and around the medial axis 8 the medial arm or medial cone 13 which gradually decreases its diameter with the distance from the medial belly 12, until it finally gets its smallest diameter when it meets the shoulder 14. Shoulder 14 is a cylindrical diameter portion, forming around axis 8 and extending further forward until it ends in the neck 18 to carry the neck 18. Neck 18 bows in FIGS. 1 and 3 to end in bridge 10 of brush head 2 to carry bridge 10 and thereby brush head 2. This configuration of the shaft or handle 1 around the medial axis 8 is an embodiment of a handle by way of example and done merely to supply a configuration of an artistic concept. The described configuration is, however, not a basic and not an exclusive kind of requirement for the proper handling of the brush head 2 and of the cleaning of the teeth and cavities by the bristles of the carriers 3 and 4. Any other suitable configuration of a handle might be applied, if so desired.

It is also possible to provide carriers 3 and or 4 with an instead of the stepwise inclination, This will be shown by FIGS. 4, 5 and 10 and other style of handles will be shown in FIGS. 4,5,6,7,10,9,12,15,18, and 20 to 27.

Figure 25:
FIG. 25 is a view onto a handle of the invention.

The above description of the handle 9 from end 19 to shoulder 14 applies also for the separately demonstrated handle of FIG. 25.

While the embodiment of FIGS. 1 to 3 has been described in general terms until now, it might also be defined, as follows:

The toothbrush of embodiment $W_1$ defining a toothbrush capable of multi-directional brushing for brushing and cleaning of teeth, gums, cavities and recesses between the outer faces of teeth, comprising in combination,
a longitudinal handle 7 elongated along a first axis, 8,
a brush head 2 forming a bridge 10 and two bristles holding carriers, 3,4,
at least partially an inclination 23, 27 between said bristle holding carriers 3, 4 and means 29 to permit at least multi-directional movements of said brush head 2 and of said bristle holding carriers, 3, 4,
whereon said tooth brush 1,2 has an imaginary longitudinal plane 20 which extends through said handle 7, said brush head 2 and said first axis, 8,
whereon said toothbrush has a second imaginary axis 9 parallel to said first axis 8 and located in said medial plane 20, while said second axis 9 may be laid to said teeth to be cleaned by said brush 3,4,5-7,15-17,
whereon a brushing space 29 is formed symmetrically of said medial plane 20 and extending from said first axis 8 to and through said second axis, 9,
whereon said brush head 2 forms a bridge 10 extending symmetrically along a portion of said medial plane, 20,
whereon said bristle holding carriers 3,4 are extended from said bridge 10 symmetrically to said medial plane 20 to form roots 30 on said bridge, 10, medial portions 25-24,28-27 extending from said roots 30 and outer portions 23,26 remote from said roots 30 and extending from said medial portions, 24,27
whereon bristles 5-7;15-17 are fastened in said carrier 3,4, to extend from said carriers, 3,4 into said brushing space, 29,
whereon said carriers 3,4 are bordering said brushing space, 29
whereon said carriers 3,4 are, at least partially inclined at different distances 25-23;28-26, from said bridge 10 under different angles of inclination, particularily at smaller angles of inclination, close to said bridge, 10 and close to said roots 30 but at wider angles of inclination, more remote from said bridge 10 and said roots 30 and more close to said outer portions 23,26, while said bristles 5-7,15-17 are preferred to extend from said carriers 3,4 at the respective distances under angles normal to said angles of inclination, of intervals and portions 25 to 23 and 28 to 26
whereby said brush head 2 can be pivoted in addition to its longitudinal and thereto normally directed movements, in order to at least partially assure the cleaning of said cavities and recesses in a direction parallel to the extension of said cavities and recesses between said outer faces of said teeth and along the respective mouthskin portions in the neighbourhood of said teeth.

FIGS. 4 and 5 demonstrate the embodiment which is most closely related to the embodiment of FIGS. 1 to 3. It shows a handle 1 with shoulder 14 and neck 18. It carries brush head 2 with bridge 10 and bristle holding carriers 3 and 4. The carriers 3 and 4 are holding the bristle tuft rows 5 to 7 and 15 to 17 respectively. Bridge 10 is somewhat stronger in these figures and the carriers 3 and 4 are in this case not stepwise inclined portioned, but they are forming archs of gradual change of inclinational angles. In the Figures, FIG. 5 shows, that the carriers 3 and 4 at their roots 30 may even incline inwardly and thereafter curving over the points of parallelity into outwardly opening archs, bordering the brushing space 29.

The handle 1 is in FIG. 3 crossing through the medial axis of the brushing space 29. This makes it especially easy to guide and pivot the brush head and the carriers properly. Handle 1 is in these figures not consisting of tapered and round cones, but of a rather wide flat bar extending substantially along the normal face 29 and thereby normally to the medial face 20 and longitudinally along the first axis 8. The axes and imaginary faces are not shown with referential numbers in these Figures, because they were already explained by means of FIGS. 1 to 3. The functioning of the brushing and cleaning is also already explained by FIGS. 1 to 3. The difference to FIGS. 1 to 3 are in these figures the replacement of the stepwise inclined carriers by the arch curved carriers 3,4; of the conical handle by the flat-bar handle 1, the different location of handle 1 and the inwards inclination of the roots 30. The inwards inclination of the roots 30 serves to an even better start of the cleaning of the bottoms of the cavities between the respective neighboring teeth at the pivotal movement of the carriers with bristles 3,4 and 5 to 7 and 15 to 17.

The embodiment of FIGS. 9 and 10 uses a single carrier 3 similar to carrier 4 of FIGS. 4 and 5. Its handle 1 is similar to that of FIGS. 4 and 5 but laterally a little shorter. Its location is in these Figures similar to that of FIGS. 4 and 5, namely provided around the normal face 21,22. The axes and faces known from FIGS. 1 to 3 are not repeated in these figures with referential numbers.

Handle 1 holds on neck 18 the bridge 10 which holds the root 30 of carrier 3. Carrier 3 has either the cross-section of that of the the arch form of FIGS. 4, 5 or that of inclined portions of FIGS. 1 to 3. In FIG. 10 it is shown of the cross-section of an arc. Carrier 3 fastens and holds the bristle tuft rows 5,6,7. The brush is pivoted with carrier 3 in the direction of the pivotal movement 32.

It is recommended to form a guide bar 31 on the opposite side of bridge 10 and extend it upwards from the bridge to border the brushing space 29. This guide bar 31 serves to guide the brush bridge 10 along the tops of the to be cleaned row of teeth. Bridge 10 and guide portion 31 may be made of plastic deformable material when so desired.

This embodiment can also be built in the symmetric form, with the carrier on the other side of the bridge 10. Guide members 31 can be disregarded if desired and it would be on the side of bridge 10, where now carrier 3 or root 30 is in FIGS. 9 and 10, when the symmetric form of the brush would be produced.

While the toothbrush of FIGS. 9 and 10 has been described above in general terms, it may also be defined, as follows:

A toothbrush capable of multidirectional brushing for brushing and cleaning of teeth, gums, cavities and recesses between the outer faces of teeth, comprising in combination, the embodiment $A_1$ consisting of a longitudinal handle 1 elongated along a first axis, 8, a brush head 2 forming a bridge 10 and at least one bristle holding carrier, 3, at least partially an inclination between said bristle holding carrier 3 and said bridge 10, and means to permit at least limited multi-directional movements of said brush head 12 and of said bristle holding carrier, 3, whereon said tooth brush has an imaginary longitudinal plane 20 which extends through said handle 1, said brush head 2 and said first axis, 8, whereon said tooth brush has a second imaginary axis 9 parallel to said first axis 8 and located in said medial plane 20, while said second axis 9 may be laid to said teeth to be cleaned by said brush, whereon a brushing space 29 is formed symmetrically of said medial plane 20 and extending from said first axis 8 to and through said second axis, 9, whereon said brush head 12 forms a bridge 10 extending symmetrically along a portion of said medial plane, 20, whereon said bristle holding carrier 3 is extended from said bridge 10 and inclined to said medial plane 20 to form a root 30 on said bridge 10, a medial portion 24 extending from said root 30 and at least one outer portion 23 remote from said root 30 and extending from said medial portion, 24, whereon bristles 5 to 7 are fastened in said carrier 3 to extend from said carrier 3 into said brushing space, 29, whereon said carrier 3 is bordering said brushing space, 29, whereon said carrier 3 is at least partially inclined at different distances from said bridge 10 under different angles of inclination, particularly at smaller angles of inclination close to said bridge 10 and close to said root 30, but at wider angles of inclination more remote from said bridge 10 and said root 30 and more close to said outer portion 23, while said bristles 5-7 are preferred to extend from said carrier 3 at the respective distances under angles normal to said angles of inclination, whereby said brush head 2 can be pivoted in addition to its longitudinal and thereto normally directed movements in order to at least partially assure the cleaning of said cavities and recesses in a direction parallel to the extension of said cavities and recesses between said outer faces of said teeth and along the respective gums portions in the neighborhood of said teeth.

In the embodiment of FIGS. 6 to 8, the carrier 3 of FIGS. 9 and 10 is replaced by a rotary or revolving carrier 37. Carrier 37 is revolvably borne on neck or bearing holder 33 and on the other end, at the tip of the brush head 2 in a bearing or holder 34. Bridge 10 has on the side opposite to the revolvable carrier 37 the guide portion or guide bar 31. Guide bar 31 includes a first bearing for bearing therein a revolvable roller 36 which is with its other end borne in a second bearing in holder 34. Holder 34 includes preferredly in its inside a gear means, for example one which includes taper gears or frictional gear means, 35,135, which serves to revolve roller 36 and rotary carrier 37 in unison. The revolvable carrier 37 holds the bristle tufts rows 5 to 7 angularly spaced around the periphery of the revolvable carrier 37 in radial direction.

The purpose of gear 35,135 is to transfer the rotation of roller 36 to revolvable carrier 37 to revolve said carrier 37 when the roller 36 revolves.

The brush of these Figures acts as follows:

Roller 36 may be of a soft material but with a non-slippery surface and is led upon the tops of the to be cleaned row of teeth. It is rolled over the row of teeth in a substantially longitudinal movement parallel to the first axis 8 of the handle 1. Thereby the roller 36 is rolling and gears 35,135 transfer this revolving movement to the carrier 37. Carrier 37 is now revolving and brushing along the row of teeth from the roots of the teeth to their tops. The bristles also enter the cavities between neighboring teeth and they are cleaning these cavities effectively.

The geometry of the brush and the location of the described parts is seen from these three Figures. It should be noted, however, that the brush could also be produced symmetrically, whereby symmetrically in this Figure as well as in the other Figures all times means, symmetrically relatively to the imaginary medial plane 20. The axes and planes are not shown by referentials in these Figures, because they are already known from the explanation to FIGS. 1 to 3.

While the toothbrush of these Figures has above been described in general terms, it may also be described as follows:

A toothbrush capable of multidirectional brushing for brushing and cleansing of teeth, gums, cavities and recesses between the outer faces of teeth, comprising in combination, the embodiment E, which consist of a longitudinal handle 1 elongated along a first axis, 8, a brush-holding head 2 and one brush holding carrier 32 provided and borne on said brush head 2,33,34 while said one carrier 37 is capable of rotation around a second axis 109 and said provision in said brush head, is provided with bearing means 33,34, to permit said rotation of said carrier, 37, whereon said means 31,36 are provided to guide said brush head along said to be cleansed teeth, and, whereon gear means 135,35 are provided to revolve said one carrier, 37, whereby said carrier 37 is capable of moving at least partially along the outer faces of the respective to be cleaned teeth in a direction substantially normal to the axes of the respective teeth; or whereon said carrier 37 is substantially a bar with a substantially cylindrical outer face, whereon bristles 5 to 7 are fastened on said carrier 37 to extend from said outer face of said carrier substantially in radial direction of said at least one carrier 37, and whereby said bristles 5 to 7 are capable of entering at least partially into said cavities and recesses between said to be cleansed teeth in order to at least, partially, brush said cavities and recesses in a directional movement substantially, at least, partially, parallel to the axes of said teeth; or wherein said one carrier 37 is of an at least partially deformable plastic material, whereby said carrier 37 is capable of brushing with its outer face the respective outer face of the respective to be brushed teeth;

whereon said means to guide said brush head on said teeth is a bridge 10 extending along said brush head 10, whereon said brush head 2 forms two lateral members 33,34 located laterally of said bridge 10 and extending from said brush head 2 in a direction substantially downward from said bridge 10, and, wherein said at least one carrier 37 is borne in said lateral members 33,34; or whereon said means to revolve said carrier is a roller 36 which is borne in said bridge 10,33,34, to be capable to revolve around its roller-axis 108, and said roller 37 has an outer face to be capable to roll along the respective portion(s) of the respective tooth(teeth) and thereby to touch said respective portion of said tooth to be set into rolling motion, when said roller 36 moves along said portion of said tooth, wherein a transmission 35 is provided to extend from said roller 36 to said carrier 37 to drive said, at least, one carrier 37 when said roller 36 rolls along said portion of said tooth or portions of said teeth, whereby said carrier 37 moves at least partially at least indirectly along the respective portion of said tooth (teeth) or said cavity (ties) or recess(es) in a direction substantially normal to the axis (axes) of the respective tooth (teeth) when said brush head 2 moves in a direction substantially parallel to the direction of said axis B of handle 7 along said teeth, while an overlaying multi-directional movement along the gum and outer face of the respective tooth can be provided, if so desired.

In the embodiment of FIGS. 11 to 13, the toothbrush head 2 has a pair of rotary brushes or revolvable carriers 40 and 41 laterally of bridge 10 and upwards from bridge 10 to border the brushing space 29 between them. The rotary carriers 40 and 41 are revolving in opposite directions and are provided to clean the different sides of a row of teeth at equal time.

While there are many possibilities for the actual building and configuration of these brushes of this embodiment of the invention, the FIGS. 11 to 13 merely are showing one single sample of actual manufacturing of this embodiment of the invention. In this sample of many different possibilities, the brush head 2 forms the bridge 10. On the lateral ends of bridge 10 the holding arms 38 and 39 are extending upwards along the brushing space 29. Each one of these arms or holders on one lateral end of the medial bridge 10. On their outer portions the holders 38 and 39 have bearings, which might be hollow cylindrical portions, to carry therein and revolvably bear therein the revolvable carriers 40 and 41. The rotary or revolvable carriers 40 and 41 have at their outer periphery the therefrom substantially radially extending bristle tufts rows 5 to 7. The rotatable carriers 40 and 41 may have endwardly extending shafts 42 or 43 with respective connection portions on their rear ends.

The outer handle or outer housing 47 may be housing a motor 46 and gear means 44,45. Gear means 44 and 45 may contain reception portions for the reception of the rear ends or portions of shafts 42 and 43 of the carriers 40 and 41. And a medial gear 46 may be fastened to the motor 46 to drive over the medial gear 46 the gearing portions 44 and 45. The figures show the convenience of thrusting the rear end connection portions or portions of shafts 42,43 of the carriers 40 and 41 just into the reception portions of the gear portions 44 and 45 of the outer handle 47. For cleaning of the bristles, the brush head 2 may in the opposite direction of the mentioned thrusting just be retracted out of reception portions 44 and 45 of the outer handle 47. For the actual use of the tooth brush of the embodiment of FIGS. 11 to 13, the controller head 48 is provided to select by turning into the control window the respective sign of operation, in the FIG. 12 it is the sign 3, for setting the desired timing, rotary speed of the brushes and carriers 40,41 and the like. The bridge 10 then guides the brush head along the tops of the row of teeth and the rotary carriers 40 and 41 are brushing the sides of the teeth with counter revolving movements, In directions from the roots of the cavities between the teeth upwards along the sides of the teeth and along the interiors of the cavities.

Up- and down-controlling gear means may be provided for example on the valve head 2 or on the bridge 10 to periodically move the carriers 40 and 41 upwards and downwards along the sides of the teeth and along the cavities between the teeth. Such gearing may also include means to lift the carriers 40 and 41 sidewards away from the teeth and cavities at the downward movements of the carriers 40 and 41, but to move them close towards the teeth and cavities at the upwards movements along the teeth and cavities. From the roots of them to the tops of them. To move along them for a proper cleaning the bristles of the revolving carriers 40 and 41. These possible modifications are, however, not shown in the drawing, because the Figures are intended to demonstrate the most simple or one of the simple possibilities of this embodiment of the invention.

While the Figures have been described above in general terms, the embodiments of the inventive matters, which reside in these figures, may also be defined, as follows; whereby it should be noted, that the motor which is housed in FIG. 12, may be utilized to drive either two carriers 40 40 and 41, or only the carrier 37, when the one-carrier brush of FIGS. 6 to 8 would be set onto the respective outer handle 47 or onto an outer handle of the like;

The toothbrush of embodiment $K_1$ which includes arrangement $E_1$ whereon a rotary motor 46 is housed in an outer body 47, which carries at least a shaft 11,38,39 which extends to said brush holding carrier 37,40,41 and, at least, indirectly connects to at least a portion of said carrier 37,40,41 to engage, at least, said portion of said carrier, whereby said rotary motor 46 transfers its rotary motion to said at least one carrier 37,40,41;

or the toothbrush of arrangement $K_1$ wherein said carrier 37,40,41 holds bristles 5 to 7 in a direction substantial radial of said carrier 37,40 or 41, whereby said bristles 5 to 7 revolve along said teeth to brush said teeth, said gums and said recesses in a direction parallel to the extension of said cavities and recesses;

or the toothbrush of embodiment K₁ wherein said rotary motor 46 is provided with an electronic control device 48 and said handle contains setting devices for defining the speed or timing of said control device;

or the toothbrush of embodiment E₁ whereon said brush head 2 forms at least two lateral members 38, 39 extending substantially laterally from said brush head 2 and laterally to said medial plane 20, whereon said brush head 2 forms a bridge 10 extending along said medial plane 20 to guide said brush head 2 along the to be cleaned teeth, wherein said carriers 37,40,41 are substantially bars with cylindrical outer faces and are revolvable boren in said at least two members, 38,39 whereon at least each one member 38 of said members 38,39 is symmetrically located opposite relatively to the other 39 of said members and relative to said medial plane 20 wherein one of said members 38 or 39 bears one of said carriers 40 or 41 another of said members bears another of said carriers, and, wherein said rotary motor 46 is provided with transmission means 46,44,45 to revolve said, at least, two carriers 40 and 41.

Figure 24:
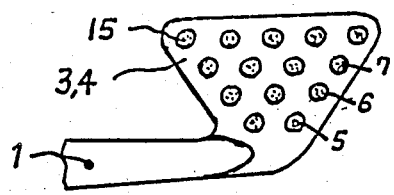
FIG. 24 is a view onto a portion of another embodiment of the invention.

FIG. 24 demonstrates the location and setting of the bristle tuft rows 5,6,7 and 15 along the side of a respective carrier. The carrier 3,4 extends from the handle 1, as usual in one or more of the other Figures of the application. The specific of the figure is, that it fulfills for a number of persons the desire of an appreciable artistic appearance, while at the same time it assures the effective cleaning of the roots of the cavities between the teeth and an effective brushing of the skin of the mouth which holds the teeth. For this purpose the outer row 15 has the maximum of number of bristle tufts 15, while the inner row 5 has the smallest number of bristle tufts 5. Therebetween are the medial bristle tufts rows 6 and 7 which are forming triangular configurations with bristles of inner triangles between bristles of neighbouring outer triangles.

In FIGS. 14 and 17 the toothbrush of this embodiment of the invention has a handle 1 with neck 18 which carries brush head 2 with bridge 10 and laterally thereon the single carrier 3 with the guide-member or guide bar 31 on the other side of bridge 10. They are extending as usual in this invention, upwards and, at least, partially along the brushing space 29 between them to border said brushing space 29. Single carrier 3 has and fastens the bristle tufts rows 5 to 7, as usual also in many other samples of carriers of this invention.

The specific value of these Figures is, that the bridge 10 consists of two bridges 49 and 50. Bridge 49 is the weaker and bridge 50 is the stronger, while both are deflectible to a limited extent. The material is respectively selected to bring the desired flexibility of bridge portions 49 and 50. When bridge portion 49 with guide members 31 is moved along the tops of the row of teeth to be brushed, it is possible by this embodiment of the invention, to provide a downwards thrust on brush head 2 and bridge portion 49. Bridge portion 49 then elongates under its flexibility and outer bridge portion 50 bows outwards, whereby the carrier 3 is inclined in a direction towards the side of the row of teeth to be brushed. The combination of the guide of the brush head by bridge 10 with members 39 and 31 along the tops of the teeth and the downwards directed thrust onto the brush head 2, it is defined with which force and in which size of inclination the carrier 3 is thrusted against the sides of the teeth, to clean them effectively. The brush of this embodiment may also be produced in the symmetrical shape, respective to the earlier described imaginary medial plane 20. This embodiment, which was above described in general terms of technology may technologically also be defined, as follows:

The toothbrush of embodiment and arrangement A₁ wherein said rootes 49 are flexible relatively to said bridge 10,49,50 wherein said bridge 10 is provided with an outer holding angle 31, whereby said holding angle 31 and said bridge 10,49,50 can be guided along said teeth and lateral dislocation of said bridge 10,49 away from said teeth is prevented by said holding angle 31, whereby said holding angle 31 acts as a guiding bar 31, wherein said carrier 3 is pivotable around said root 49,50, by said flexibility of said root 49 with outer bow 50, wherein a thrust-transfer means 49,50 associated to said carrier 3 and to said bridge 10,49,50;

whereby thrusting movements on said bridge 10,49, in a direction towards said teeth are transfered by said transfer means to said carrier 3 to pivot said carrier 3 in a direction substantially normal to the direction of said thrusting movements toward the sides of said teeth and into the cavities between said teeth to enter said cavities with force and to move along said sides of said teeth with a force which is determined by the force of said thrusting movements on said bridge 10,49,50.

FIGS. 15 and 18 are demonstrating one of the most simple and inexpensive toothbrushes of the invention, and thereby one of the simplest embodiments and arrangements. It has a handle 1 with a brush head 2. Brush head 2 is formed in its cross-section, shown in FIG. 18, by an arch or bow or as in FIG. 3, by a stepwise inclination. The brush head 2 directly forms the carrier 3 with the therein fastened and therefrom upwardly towards brushing space 29 extending rows of bristle tufts 5, 6 and 7. The bow or arch configuration of carrier 3 is formed for example with a constant radius 51 around centre axis 52 below the carrier 3.

Thus, the brush of this embodiment is generally similar to the flatplate common tooth brush however with the feature of the invention, that the arch configuration of the cross-section of the carrier 3 permits a proper pivotal movement from the bottoms of the teeth and of the cavities between the teeth upwards along said teeth and cavities in order to clean them properly and at all times substantially with bristles properly directed towards cavities. The unproper bowing of bristles of brushes of the prior art and their sliding along with their outer faces without brushing and cleaning effect is thereby prevented. In order to properly handle the pivotal movement and also in order to have an inexpensive brush, the handle 1 may be in its cross-sectional area configurated similar to that of the brush head or carrier 2,3. This embodiment of the invention may also be defined as follows:

A toothbrush comprising a handle 1 with a brush head 2 on one end of said handle, wherein said brush head constitutes a bristle holding carrier 3 with the crosssectional configuration of downwardly inlined sides and bristles 5,6,7 extending upwards from said carrier 3 in directions normal to said cross-sectional configuration, whereby said toothbrush permits a pivotal movement along the teeth and cavities between them with properly directed bristles 5–7 for an effective brushing and cleaning of said teeth and cavities.

FIGS. 16 and 19 are showing an embodiment for the most effective cleaning of the teeth and cavities. It is motor-driven in the Figure, but could also be hand-operated, if properly designed for such a purpose. In the outer body or outer handle 47 the portion 53 is the gearing portion to handle the carriers 3 and 4 and their respective shafts or arms, also shown by 3 and 4. Outer handle 47 also houses the motor 46. In these and the other respective figures the motor 46 may be an air-driven motor, a gas-driven motor, a fluid-driven motor or an electrically driven motor. A control handle 48 can be provided to define the desired movement, timing and/or speed of the movements of the carriers 3 and 4. Such movements may be set in relation to the medial plane 20 and to the bridge 10. In FIG. 16 the setting control window shows operational control function 5.

The FIG. 19 below FIG. 16 explains one of the preferred movement-cycles of the invention in relation to a tooth 54 in the respective portion 55 of the mouth.

In actual use, the following actions and movements can occur as an example of the many other possibilities:

Bridge 10 guides the brush head 2 on the upper tops of the teeth 54. The carriers are providing the motions 56 to 59 along the sides of the teeth. For example, carriers 3 and 4 are moving with their bristles 5 to 7, 15 to 17 at equal times towards the teeth 54 as shown by arrows 57 and 59. Thereafter they are moving upwards along the sides of the teeth 51 and upwards in the respective cavities between neighbouring teeth 54. This movement is shown by arrows 56 and 58. After completion of this cleaning and brushing cycle the carriers 3,4 are moving away from the sides of the teeth in directions contrary to arrows 57 and 59. Thereafter the carriers are moving downward again in directions contrary to arrows 56 and 58, whereafter they are starting the cycle again with movements along arrows 57,59.

This movement may have an overlay of a pivotal movement, when the respective carriers 3 and/or 4 have the different inclinations or arch forms of the respective other figures. Instead of handling two carriers 3 and 4, the movements may be done with a single carrier 3 or 4 when only a single one of the carriers 3 or 4 is applied.

Figure 21:
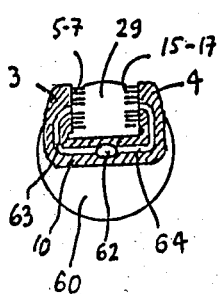
FIG. 21 is a cross-sectional view through FIG. 20 along the line XX—XX.
Figure 22:
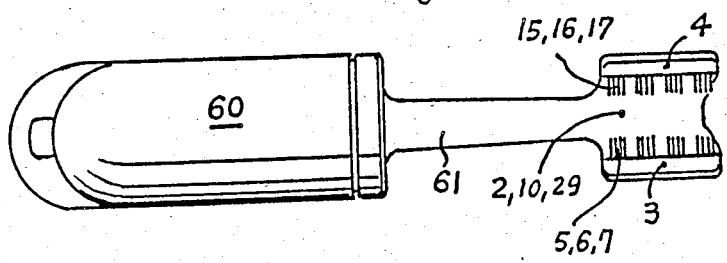
FIG. 22 is a view from top onto FIG. 20.

FIGS. 20 to 22 demonstrate an embodiment of a tooth-brush of the invention, which includes an outer handle 60 which houses at least one containing chamber for the reception of a fluid or of a medicine. Container 60 is communicated to a passage 62 through the medial handle portion 61 which may branch in brush head 2 into multiple branches which finally end in at least one exit port or a plurality of exit ports 65. The exit ports 65 may be located in the bridge 10 or in the interior sides of the carrier(s) 3 or 3 and 4 and they are porting open towards the brushing space 29. The twin- or branch-passages are seen in FIG. 21 by passages 63 and 64. The at least one carrier 3 or the plurality of carriers 3 and 4 are holding the therein fastened bristle tufts 5 to 7 or 15 to 17 respectively as already known from the other Figures. The fluid and/or medicine may be transferred to the ports 65 by squeezing the container and outer handle 60 or by a motor in the outer handle 60. The passing of fluid and or of medicine out of the ports 65 or of a single port 65 may be done separatedly or by a combined device which supplies the medicine in a defined ratio relatively to the ratio or rate of flow of the fluid passed out of the at least one exit port 65. Mixing of fluid and medicine may be done accordingly.

Figure 23:
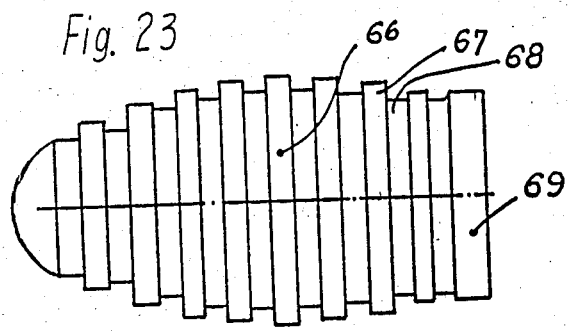
FIG. 23 is a view onto an embodiment of a deflectible container in the invention.

FIG. 23 demonstrates a respective outer handle 60 with is made of a deflectible outer skin with radial strengtheners 67 around the skin portions 68. They are serving to return the outer handle 66 to its original size after the skin 67,68 of container 66 has been depressed radially inwardly to press the contained fluid or medicine through the respective at least one passage 62 into the brushing space 29 and onto the teeth and cavities. A connection portion 69 is provided on one end of outer handle 66 to be able to receive and connect a respective medial handle 61 with connecter portion 166.

The configurations shown are by way of example only, and respective means may be applied in combination with one or more of the other Figures, for example to those with motors or with other carriers of others of the figures and embodiments or arrangements.

FIGS. 25 to 27 are supplied to show some convenient handles for the toothbrush. Their specific value is to supply a configuration of a comfortable artistic appearance.

In addition, however, they may also serve technological purposes. For example the outer foot 11 of FIG. 25 is a cone, enlarging its diameter parallel to the distance from the rear end 19 towards the medial belly 12. This makes the handle of this Figure very applicable for an insertion into a respective reception recess in a respective outer handle or outer body or outer container of one or more of the other Figures. The rear end 19 is in this Figure the half of a ball in order to provide a proper thrust-portion for a forced release of the outer foot 11 out of a respective reception and holding recess or space in an outer handle. The medial arm or medial cone 13 thins towards the mostly cylindrical shoulder 14. On it the respective brush head of one of the figures of the application or of the prior art may be borne or extend therefrom.

The handle of FIGS. 26 and 27 has, aside from its enjoyable artistic configuration, the technological purpose of providing a proper holding in the hand of the respective person for the proper guidance of the several movments of the brush heads of the invention, and, specifically of the pivotal movement of the present invention.

It may be noted, that the specification shows a number of embodiments and arrangements of the invention, but what can be done with them by the combination of one or more with others may for example be defined as follows:

A toothbrush,
  wherein said handle 60,47 contains a chamber 47,60,160, said chamber 47,60 contains at least a teeth-health medicine and a passage 62 from said chamber to port into said brushing space 29,
  wherein said motor 46 is connected to means to at least temporarily, stepwise or continually transfer at least defined portions of said teeth-health medicine to and through said carrier 34,37,40,41 to supply it respectively to the to be cleaned portions of said teeth, cavities, recesses and gums;

or a toothbrush, for example of FIGS. 12, 16 or 20,
wherein said handle 47,60 contains a second chamber 260 for the reception and containment of a fluid,
wherein said chambers 160,260 are communicated to passages 62, which communicate to each other, and,
wherein said motor 46 is provided with means to press said medicine and said fluid in properly to each other related portions through said passages 62,63,64 and carrier(s) 3,4,37,40,41 to said teeth, cavities, recesses and gums when said toothbrush is used to clean or cleans said teeth, cavities, recesses and skin;

or a toothbrush, for example of FIGS. 6 to 8, 11 to 13, 16 and 19,
wherein said motor 46 is provided with control means 46 and said handle with a setting means 48 for the adjustment of said control means, and,
wherein said setting means 48 is capable of a predetermined or variable setting of said control means to define the rotary speed of said carrier 3,4,37,40,41 and the quantities and advance ratios of said medicine and of said fluid;

or a toothbrush, for example of FIGS. 4 and 5
whereon said handle 7,61 includes an elongated rear and main-portion extending parallel to said first axis 8 and to said third axis 21,22 and substantially along a fourth axis 208 through the middle of said arch plate 3,4 of said carrier 3,4 and thereby substantially along the middle between said first and third axes 8,9,21,22,
whereby the holding portion substantuated by said rear and main portion of said handle 1 provides the center axis of pivotal movement through said arch plate 3,4 for effective and convenient brushing of said cavities between said teeth;

or a toothbrush
whereon said handle 1,38,39 includes a rear portion 11,42,43 and an outer body 47,60 is associated to said tooth brush, wherein said outer body 47,60 houses a motor 46 and contains a holder 44,45, wherein said holder 44,45 retains and holds said rear portion 42,43 of said handle 11,38,39, and,
wherein said motor 46 drives said pivotal movement of said tooth brush around said fourth axis, when said toothbrush is held in the hands of the person who cleanes its teeth and said motor 46 is set to run and to drive said pivotal movement and thereby said pivotal movement for cleaning of said cavities between said teeth;

or a toothbrush
wherein said rotary motor 46 is a fluid motor,
wherein said outer body 47,60 is provided with an entrance port to make it possible to connect said entrance port by a flexible hose to the water pipe in the bathroom where the cleaning of the teeth occurs, and wherein said entrance port communicates to said motor,
wherein said hose transfers water from said pipe to said motor 46 and through said motor, whereby said motor is revolved, and,
wherein an exit port extends from said motor into a passage 62 through said handle 61,39,38 and through said carrier 3,4,37,40 or 41,
whereby said water flows through said bristles 5-7, 15-17 towards said teeth, cavities, recesses and skin, when said motor is revolved and said teeth are brushed by said toothbrush.

FIGS. 28 and 29 are longitudinal sectional views through devices which have a fluid motor 46 assembled in a housing or holder 47. These devices are preferred in this specification to be utilized as toothbrushes wherein the fluid motor in the handle of the toothbrush drives a movement or a plurality of movements of the toothbrush which may be inserted into the outgoing shaft 100 of the device. The sectional FIGS. 30 to 33 illustrate details of FIGS. 28 and 29. FIGS. 30 to 33 are cross sectional Figures either through FIG. 28 or through FIG. 29 respectively. Because at those places where the cross sectional views of FIGS. 30 to 33 are taken in FIG. 28 or in FIG. 29, both Figures, namely FIGS. 28 and 29, are equal. In detail FIG. 30 is a cross-sectional view through FIG. 28 or through FIG. 29 along the arrowed line A—A of FIGS. 28 and 29. FIG. 31 is a cross sectional view along the arrowed line B—B of FIGS. 28 and 29. FIG. 32 is a cross sectional view through FIG. 28 or 29 along the arrowed line D—D of FIG. 28 or 29 and FIG. 33 is a cross sectional view through FIG. 28 or through FIG. 29 along the arrowed line C—C of FIG. 28 or of FIG. 29.

In FIGS. 28 to 33 or in one or more of these Figures, the connector 175 is a portion of the stationary control body 75 which is fastened in the housing or handle 47. The connector portion is provided with a radial widening 750 to be able to keep the fluid hose like the water hose or air hose thereon. The fluid hose may be a hose set onto the common water pipe of the common household. The fluid which commonly leaves the fluid pipe, for example, of the household, with a certain pressure, flows through the passage 102 of the connector portion of the control body 75 and through a portion of the control body to and through the control port 175 of the stationary control body 75 into and through the rotor passage 200 or through one or more thereof into the working chamber or working chambers 78 of the rotor assembly 46. Thereby the pressure in the fluid tends to enlarge the volume of the respective working chamber(s) 78 whereby the rotor assembly 46 is forced to revolve around the axis of the control body 75. The direction of revolution of the rotor assembly 46 is seen in FIG. 30 which shows that the working chambers 78 increase their volumes over control port 175 if the rotor 176 revolves in clockwise direction in FIG. 30. This Figure also shows that the actuator ring or stroke guide ring 79 has an inner face which is farther distanced from the outer diameter of the rotor 176 at the bottom portion in FIG. 30 than in the top portion of FIG. 30. Since on the right side of FIG. 30 the rotor passages 200 are communicated to the control port 175 which has the pressure of the fluid which flows through port 175 and through passages 200, the pressure in the fluid forces the working chambers 78 in the right portion of FIG. 30 to enlarge their volume what they can do by revolving the rotor 176 with its vanes 77 in the clockwise direction in FIG. 30. At such revolution of the rotor assembly the respective working chambers 78 on the left side of FIG. 30 decrease their volumes and pass the respective amount of fluid through the respective rotor passages 200 on the left side of the respective Figures into and through the outflow control port 174 of the stationary control body 75.

The outflow control port 174 of the stationary control body 75 extends into an outflow passage through the rear portion of control body 75 to end in the rear portion of control body 75 in an outflow control port 202. This control port 202 has the form of an arch of less than 181 degrees and is seen specifically in FIG. 31. The rear end of control body 75 forms an end face which is a stationary control face for control of axially directed flow. Compared thereto the outer diameter of the control body 75 is of cylindrical configuration and forms a control face for radially directed flows with control ports 174 and 175 in the control face. It is to be noted that the left portion of FIG. 31 does not have any control port.

The rotor assembly 46 is associated to a rotary member 146. This is done in FIG. 28 thereby, that the rotary member 146 forms a portion on the rear end of the rotor assembly 46 or of end walls 76 thereof. In FIG. 29 the association of the rotary member 146 to the rotor assembly 46 may be done by clutch means 80. The rotor assembly of FIG. 29 may also have axial thrust faces 81 which are, however, in the assembly of FIG. 29 not utilized for the operation of the toothbrush.

The rotary member 146 forms close to its front portion a rotary face which is complementary relative to the control face of the rear portion of the stationary control body 75 and which slides along the rear control face of control body 75 and seals therealong. This is true for FIG. 28 as well as for FIG. 29, but in FIG. 29 the stationary and rotary faces of control body 75 and of rotary member 146 form a straight line normal to the axes of the stationary control body 75 and of the rotary member 146. This straight line defines the closeness and the sealing of the stationary control face and of the rotary control face of the rear end of the stationary control body 75 and of the front end of the control portion of rotary member 146. The rotary member 146 is provided with a cylinder and a piston therein. The rotary cylinder has an axis which is again normal to the axis of the rotary member 146. The piston 86 divides the cylinder into cylinder spaces 85 and 87 and extends with a piston shaft 88 radially through one portion of the rotary member 146. The piston 86 with its piston shaft 88 is reciprocable in the cylinder spaces 85 and 87. Flow control passages extend from the cylinder chambers axially through the respective front portion of the rotary member 146 to and through the mentioned rotary control face of rotary member 146. Flow control passage 82 extends axially directed frontwards from cylinder space 87 and flow control passage 83 extends axially directed frontwards from cylinder space 85. The front ends of passages 82 and 83 are running accordingly over the stationary control face of the rear end of control body 75 whereby they at a little less than half a revolution alternately communicate with control port 202 as is specially visible in FIG. 31. At the other portion of a revolution, namely slightly more than half of a revolution of the rotary member 146 the respective passage 82 or 83—see FIGS. 31 and 33—is closed by that portion of the control body 75 which has no part in FIG. 31. Thus, when the medial rotary member 146 revolves, the fluid which flows from port 174 through port 202 flows during about slightly less than half of a revolution into passage 83 and therethrough to enter into the cylinder space 85 and thereby to press the piston 86 leftward in FIGS. 28 and 29. At the other half of the same revolution or at slightly less than a half revolution, the fluid which flows through ports 17 and 202, flows into and through the passage 82 into the cylinder space 87 to press the piston 86 rightward in FIGS. 28 and 29. Thus, at each revolution of rotary member 146, the piston 86 moves once to the right and once to the left in the cylinder spaces 85 and 87. At those times when the piston 86 moves to the left the fluid in space 87 can not flow through passage 82 and is thereby forced to flow rearward through passage 93 since the space 87 decreases its volume when the piston 86 moves to the left. At the other half of the revolution when the piston 86 moves to the right as described, the chamber 85 decreases its volume, and, since the fluid can not escape through the then closed passage 83, the fluid from the its volume decrasing space 85 is pressed rearward through passage 92. Passages 92 or 93 which are provided to extend rearward from the respective cylinder space 85 or 87 may be provided with flow resistance valves 205 or they may combine to a single passage. In FIGS. 28 and 29 the passages 92 and 93 combine to a single passage with a flow resistance valve 205 therein which is loaded to keep the closed position by a spring 206. Spring 206 is of such a little force that the valve 205 opens at a pressure which is smaller than the pressure in the ingoing passage 102. But the force of the spring 206 is strong enough to secure that the fluid maintains a minimum of pressure which is strong enough to force the piston 86 to reciprocate as described in the spaces 85 and 87. When the valve 205 opens the fluid which flows from the ingoing passage 102 through the device as described herebefore, flows on into the passage 99 in the outgoing member 100. Passage 99 may form a seat as, for example, a cone, to keep therein the thereinto insertable handle of the respective hollow toothbrush to transfer the fluid to the bristles of the toothbrush.

The rotary member 146 is revolvably borne in a bearing portion 180 in the housing 47. The bearing portion itself is stationary provided in the housing and forms a hub (a medial bore) to bear therein the mentioned rotary member 146. From the hub or bore an annular recess 203 extends radially outwardly into the bearing portion 180 to provide a ring 204 therein which is able to move radially in the mentioned recess 203. The inner face of ring 204 is laid radially of the piston shaft 88 whereby the piston shaft 88 presses the ring 204 in recess 203 leftward at those times when the piston 86 moves to the left as described. The outer face of ring 204 then presses against the finger tip 191 of the swing arm 90. The thrust spring 192 on the opposite radial end of finger tip 191 presses the finger tip 191 again to the right in FIGS. 28 and 29 at those times when the piston 86 moves to the right in these Figures. The swing arm 90 is swingably borne by a bearing pin 91 in a holding portion 95 and in a recess 190 as seen in FIGS. 28, 29 and 32. Thus, at each revolution of the rotary member 146 the piston 86 permits the spring 192 to force the finger tip 191 of lever 90 to the right while at some time of the same revolution the piston 86 forces over its shaft 88 and ring 204 the finger tip 191 of lever or arm 90 to move to the left in FIGS. 28 and 29. Whether the ring 204 rotates and reciprocates or only reciprocates in recess 203 is immaterial and a question only thereof whether the friction is higher on the inner face or on the outer face of ring 204.

The device is also provided with a second bearing portion 95 or 195. In FIG. 28 this portion 95 is stationary while it is rotary in FIG. 29. It has a spheric inner face wherein a spherically—which means ball part formed—swing head 96 or 966 of the outgoing shaft 100 is swingably borne. A portion of the outgoing shaft is rearwardly of the bearing portion 95 or 195 surrounded by a ring member 210 which is over pins 211 and connecting blades 98 connected to the rear end of the swing arm or swing lever or transfer lever 90 to the rear portion 97 of said lever or arm 90. Thus, when the finger tip 191 of the front portion of lever 90 reciprocates from the right to the left in FIGS. 28 and 29 the rear portion with its connector 211 reciprocates in the opposite direction since the medial portion of lever 90 is swingable or pivotably borne by bearing 91 in member 95 or housing 47. Since the rear or outgoing shaft 100 is able to swing or to pivot around the center point of its ball part formed rear end in the bearing 95 or 195, the connectors 98,211 and ring 210 transfer the reciprocal movement of the rear arm portion 97 to the respective portion of the outgoing shaft 100 and to the tooth brush if it is assembled into shaft 100. Thereby, when the fluid flows through the device the outgoing shaft 100 reciprocates and the toothbrush can thereby clean the cavities, gums and teeth. To prevent fluid to flow or leak out of the housing 47, the flexible seals or a flexible seal 101 may be provided in the rear cover 102 of the housing 47.

Thus, both, the outgoing shafts 100 of FIGS. 28 and 29 reciprocate in a swing movement around the centers of their rear ball ends, if water or fluid fluid flows through the device. In FIG. 28 this described reciprocational swing of shaft 100 is the sale movement of shaft 100. But in FIG. 29 the reciprocal swing movement is overlaid by a rotary movment of the outgoing shaft 100. For that purpose in FIG. 29 the rear ball portion 96 of shaft 100 is borne in a rotary bearing body 280. This rotary body 280 is borne in the stationary portion 180. Body 280 is provided with axially extending recesses whereinto pins 213 extend, which are provided in the rotary member 146 to extend axially therefrom into the mentioned recesses in body 280 to engage the body 280 force the body 280 to revolve in unison with the rotary member 146. A respective pin 208 extends substantially radially from the ball formed rear end of shaft 100 into a recess 207 in rotary body 280 whereby the rotary body 280 forces over the recess 207 and pin 208 the portion 96 or 966 and shaft 100 to revolve in unison with the rotary body 280 and the rotary member 146 as well as in unison with the rotary assembly 46 of the motor of the device.

Thus, while FIG. 28 provides a reciprocating swing of the outgoing shaft 100, the FIG. 29 provides a reciprocating swing together with a rotary movement of the outgoing shaft 100. If the reciprocation of piston 86 is blocked, stopped, for example, by distance rings which are illustrated by dotted lines without referential numbers in FIG. 29, the outgoing shaft 100 of FIG. 29 will do solely a rotary movement without any further additional movement. The same affect is obtained if the piston 86 is left away and the cylinder chamber 87 is radially closed or if the cylinder chambers 85 and 87 are not provided or other means are set to transfer the fluid or to pass the fluid from control port 174 to passage 99. The simplest device for rotary movement of shaft 100 without additional movement would be to extend the rotary member 140 rearwards to provide the outgoing shaft 100.

Thus, in summary, the devices of FIGS. 28 to 33 may be used either; to drive:
(a) the rotary movement of a toothbrush;
(b) the reciprocal or pivotal movement of a toothbrush;
(c) the rotation and swing of the toothbrush;
(d) the revolution of an outgoing shaft of a device;
(e) the reciprocal swing of an outgoing shaft of a device, or ;
(f) the rotation and reciprocal swing of an outgoing shaft of a device.

Respective to FIGS. 28 to 33 also the following may be of interest:

The radially inner face of the actuator member 79 defines the locally different radial size of working space 78 at different angular locations and thereby the during a revolution periodic increase and decrease of the volumes of the individual working chambers of working space 78. The mentioned individual working chambers are provided adjacent to the displacement members 77 and sealed by them. Each displacement member 77 is provided to at least one single individual working chamber of working space 78, for example, as known from my U.S. Pat. Nos. 2,975,716; 3,223,046 or others.

The control body 75 also has the function to control with its cylindrical outer face and control parts therein the flow of fluid to and from the working space 78 and its individual chambers, as for example is known from my U.S. Pat. No. 3,062,151 or others.

Members 209 and 215 hold members 95, 180 and 280 axially in place.

What is claimed, is the following:

1. A device which has chambers which are able to contain fluid, wherein inlet means and outlet means are provided to lead fluid to and away from said chambers, said chambers are provided to a rotor which is revolvably borne in said device and surrounded by a stroke guide for guiding the increase and decrease of said volume of said chambers in combination with means to periodically at each single revolution of said rotor to increase and decrease the volumes of said chambers, individually for each of said chambers when fluid flows through said chambers, said device contains also a medial portion, a shaft with said shaft pivotally borne in the housing of said device, a control body to control the flow of said fluid to said chambers, a transfer arrangement and an improvement with said improvement comprising, a combination, wherein said transfer arrangement includes a transfer lever which is swingably borne substantially by its medial portion on a bearing in the housing of said device while said lever has two ends with one of its ends subjectable to thrust by a piston rod and the other of its ends connected to said shaft, wherein said medial portion is provided with a rotary member, wherein a radially extending space is provided in said rotary member with a reciprocable piston provided in said space with a piston rod extending from said piston through a portion of said space and through a portion of said rotary member outwards of said rotary member to be able to engage a ring provided between said piston rod and said one end of said lever, and, wherein said rotary member is provided with ports and passages to transfer fluid from one of its ports to one end of said space and from the other of its ports to the other end of said space when said ports revolve over respective control ports which are provided on said control body, by which said fluid in said ends of said space provides thrusts onto the ends of said piston to press said piston towards one end of said ends of said space and thereby to press said piston rod against said ring, said ring against said one end of said lever to swing said lever whereby the other end of said lever pivots said shaft in said housing of said device.

2. The device of claim 1,
wherein said shaft is with one of its ends pivotably borne in a pivot center in said housing and said transfer arrangement pivots said shaft around said pivot center.

3. The device of claim 1,
wherein said control body is provided with a connection,
wherein said connection can be fixed to a hose,
wherein said hose can be fixed to the water pipe in the common household,
wherein said fluid is water supplied from said water pipe, and,
wherein said shaft is connected to a toothbrush, whereby said toothbrush reciprocates and may be used for cleaning of teeth and cavities therebetween, when said device is held in the hand of a person.

* * * * *